United States Patent [19]
Groh et al.

[11] Patent Number: 5,753,269
[45] Date of Patent: May 19, 1998

[54] OTIC MICROBIAL COMBINATIONS

[75] Inventors: Michael Groh, Lee's Summit, Mo.; H. Dennis McCurdy; Francisco A. Cabrera, both of Overland Park, Kans.

[73] Assignee: Bayer Corporation, Pittsburgh, Pa.

[21] Appl. No.: 579,461

[22] Filed: Dec. 27, 1995

[51] Int. Cl.$^6$ ................................................ A61K 33/38
[52] U.S. Cl. ................................................ 424/618
[58] Field of Search ................................................ 424/618

[56] References Cited

U.S. PATENT DOCUMENTS

| | | | |
|---|---|---|---|
| 3,761,590 | 9/1973 | Fox, Jr | 424/228 |
| 4,404,199 | 9/1983 | Bonaldi et al. | 424/238 |
| 5,374,432 | 12/1994 | Fox, Jr. et al. | 424/618 |

FOREIGN PATENT DOCUMENTS

| | | |
|---|---|---|
| 337328 | 10/1989 | European Pat. Off. |
| 85/01208 | 3/1985 | WIPO |

OTHER PUBLICATIONS

J Burn Care Rehabil. Jul.–Aug. 1988 9 (4) pp. 359–363, United States XP000670922 Modak S.M. et al.

Vet. Clin. North Am. Small Anim. Pract., Sep. 1994, 24/5 (921–952) USA, XP000670927 Rosychuck R.A.W. pp. 932–940.

Tijdschr Diergeneeskd, Mar. 15, 1982, 107 (6) p224–8 Netherlands, XP000671011 Vand Den Bogaard AE et al:.

Der Praktische Tierarz, vol. 67, No. 11, (month unavailable) 1986, pp. 963–966, XP000671012, A.E.J.M. Vand De Bogaard et al.

J. Antimicrob Chemother, Sep. 1990, 26 (3) P303–5, England, XP000670914 Elies W.

J. Trauma, Jan. 1985, 25/1 (27–31), USA XP000670884 Modak S. et al.

Bogaard et al, Dep. Med. Microbiol., Univ. Limburg, Netherlands (1982–Month unavailable) pp. 224–228.

*Primary Examiner*—Zohreh Fay
*Attorney, Agent, or Firm*—Joseph C. Gil; Godfried R. Akorli

[57] ABSTRACT

Disclosed herein is an otic composition that is useful in treating otic infections comprising an antimicrobial such as a quinolone or a salt thereof and silver sulfadiazine in a therapeutically effective combination to treat otic infections in animals.

3 Claims, No Drawings

OTIC MICROBIAL COMBINATIONS

BACKGROUND OF THE INVENTION

1. Field of Invention

The present invention relates to otic formulations and antimicrobial agents and more specifically to otic formulations containing a combination of antimicrobials such as quinolones and silver sulfadiazine.

2. Brief Description of the Prior Art

U.S. Pat. No. 4,404,197 discloses the use of certain quinolones and silver sulfadiazine in treating burns. More specifically, the patent discloses compositions that include silver sulfadiazine and 1-ethyl-6-fluoro-1,4-dihydro-4-oxo-7-(1-piperazinyl)-3-quinolone carboxylic acid or its metal salts, e.g., silver, zinc, cobalt or cerium salts. Distinctly, the patent teaches the use of these compositions in treating burns, and in combating topical, surface or skin infections, including microbial and fungal infections and the like. However, the patent fails to teach or suggest the use of the compositions for otic applications.

U.S. Pat. No. 3,761,590 discloses the use of silver sulfadiazine alone in burn therapy. Silver sulfadiazine, preferably in a water-dispersible hydrophilic carrier, is applied to the burn.

Bogaard et al. Dep. Med. Microbiol., Univ. Limburg, Netherlands discloses the use of silver sulfadiazine cream in treating chronic Pseudomonas infection of the external auditory canal in dogs.

As would be realized, there is a need for an effective composition for treating otic infections. The present invention provides a therapeutically effective combination of active ingredients that are useful in treating otic infections.

SUMMARY OF THE INVENTION

In accordance with the foregoing, the present invention encompasses a composition that is useful in treating otic infections in animals, said composition comprising a therapeutically effective combination of an antimicrobial such as an antibacterial agent which preferably a quinolone or a salt thereof, and silver sulfadiazine. The invention further encompasses the use of a composition comprising a therapeutically effective combination of an antimicrobial such as an antibacterial agent which is preferably a quinolone or a salt thereof, and silver sulfadiazine in treating otic infections.

Also, encompassed by the present invention is a process for treating otic infections by administering the composition to animals, particularly, small animals such as dogs. The composition containing a combination of an antimicrobial such as an antibacterial agent which is preferably a quinolone and silver sulfadiazine can be administered as such or with a physiologically acceptable carrier such as an oil in water emulsion.

The composition can be used to safely and efficaciously treat otic infections such as infections of the outer ear canal. In particular, the composition can be used to treat infections caused by the bacteria Pseudomonas, or fungus, Malessezia pachydermitis. The invention is described more fully hereunder.

DETAILED DESCRIPTION OF THE INVENTION

As set forth above, the present invention relates to a composition that is useful in treating otic infections. The composition comprises a therapeutically effective combination of an antimicrobial such an antibacterial agent which is preferably a quinolone or a salt thereof and silver sulfadiazine. Typically, the quinolone is a fluorinated quinolone. The effective combination is described hereunder with specificity as to quinolones. The invention, however, encompasses combinations of silver sulfadiazine and other antimicrobial which can combined with the silver sulfadiazine to provide effective treatment of otic infections in the manner of the combination of silver sulfadiazine and quinolones. Non-limiting examples of the fluorinated quinolone can be selected from the group consisting of Enrofloxacin; 6-Fluoro-1,4-dihydrodihydro-1-(methylamino)-7-(4-methyl-1-piperazinyl)-4-oxo-3-quinolonecarboxylic acid (Amifloxacin); Benofloxacin; 6-Fluoro-1-(4-fluorophenyl)-1,4-dihydro-7-(4-methyl- -piperazinyl)4-oxo-3-quinolonecarboxylic acid (Difloxacin); Flerofloxacin; 6,8-Difluoro-1-(2-fluoroethyl))-1,4-dihydro-7-(4-methyl-1-piperazinyl)4-oxo-3-quinolonecarboxylic acid (Fleroxacin); 1-Ethyl-6,8-difluoro-1,4-dihydro-7-(3-methyl-1-piperazinyl)4-oxo-3-quinolonecarboxylic acid (Lomefloxacin); Marbofloxacin; 1-ethyl-6-fluoro-1,4-dihydro4-oxo-7-(piperazinyl)-3-quinolonecarboxylic acid (Norfloxacin); 9-Fluoro-2,3-dihydro-3-methyl-1 0-(4-methyl-1-piperazinyl)-7-oxo-7H-pyrido[1,2,3-de]-1,4-benzoxazine-6-carboxylic acid (Ofloxacin); Perfloxacin; Rufloxacin; Sarafloxacin; and Temafloxacin. The fluorinated quinolone preferred herein is Enrofloxacin. U.S. Pat. No. 4,556,658 which is incorporated herein by reference provides an illustrative but non-limiting description of the quinolone with particularity to Enrofloxacin and a method of preparing the same.

The quinolone or the salt thereof and the silver sulfadiazine are employed in an amount sufficient to provide a composition that would be pharmaceutically effective. The quinolone or the salt thereof can be employed in an amount of 0.005 to 1.5 percent by weight of the composition and preferably 0.1 to 1 percent by weight of the composition. Silver sulfadiazine can be employed in an amount of 0.05 to 2 percent of the composition, and preferably in an amount of 0.5 to 1.5 percent of the composition.

In the preparation of the composition, the quinolone and silver sulfadiazine can be combined in any convenient manner. For example, comminuted silver sulfadiazine and the quinolone can be mixed with each other. The composition can be used directly or preferably in formulation with a pharmaceutically acceptable physiological carrier.

A non-limiting example of a pharmaceutically acceptable physiological carrier can be an oil in water emulsion. Typically, the oil is a non-irritating emollient oil. An illustrative but non-limiting example thereof can be selected from the group consisting of a mineral oil, vegetable oil and a reformed vegetable oil of known composition. More specific but non-limiting examples of the oil can be selected from the group consisting of peanut oil, sesame seed oil, cottonseed oil, etc.; a medium chain ($C_6$ to $C_{12}$) triglycerides (e.g., Miglyol Neutral Oils 810, 812, 818, 829, 840, etc.) available from Huls America Inc. Typical emulsifiers employed herein can be selected from the group consisting of Span 60 which is sorbitan monostearate and Tween 60, which is Polysorbate 60 (both of which are available from ICI Americas). Preferably, the emulsifiers are nonionic. The emulsifiers can be employed in an amount of 1.5 to 6.5 percent by weight of the composition and preferably 3.0 to 5.0 percent by weight of the composition. The hydrophobic phase of the emulsion can be in an amount of 15.0 to 25.0 percent by weight of the composition and preferably 18.0 to 22.0 percent by weight of the composition.

It is a distinct feature of the invention that the composition of the invention can be formulated as an emulsion base comprising oil in water emulsions described herein. Heretofore, silver sulfadiazine had been formulated as a cream base or a solid synthetic dressing for use in burn therapy. Related silver nitrate solutions were considered undesirable.

In addition to the above components, a formulation of the composition of the invention may contain other components such as preservatives (benzyl alcohol, parabens, or benzoates), stabilizers (cetyl stearyl alcohol, glycerol esters), odor masking agents, and coloring agents.

The following is an illustrative but non-limiting description of a method of providing the compositions of the invention. In a properly equipped vessel, an emulsifier and a fatty acid alcohol are heated in an oil to form a suspension, and the active ingredients are added to the suspension. In a different vessel, an emulsifier is added to hot water to form an aqueous solution. To the solution are added a preservative and the suspension with vigorous mixing. The resulting mixture comprising the composition of this invention is effective in treating otic infections.

In treating an otic infection, the composition is preferably administered by applying it topically in a pharmaceutically effective amount. The composition can be applied at a dose of five to twenty drops per ear and preferably at a dose of eight to twelve drops per ear as needed to coat the ear canal. The composition can be applied twice a day.

This and other aspects of the invention are further illustrated by the following non-limiting examples in which all parts and percentages are by weight unless otherwise specified.

EXAMPLES

The following examples illustrate the otic compositions of the present invention and methods of preparing and using the same. In the present embodiment of the invention, the silver sulfadiazine and the quinolone are combined as follows.

Polysorbate 60 (Tween 60) was added to water in an SS jacketed tub at a temperature of 50° to 60° C. The resulting aqueous solution was heated to 61° to 75° C. At a temperature of 66° C., a preservative (benzyl alcohol) was added to the aqueous solution while mixing three to ten minutes.

At a temperature of 75° C. Enrofloxacin and silver sulfadiazine were added to Mygliol Oil in a separate vessel over a period of three to five minutes. Sorbitan Monostearate (Span 60) and cetyl stearyl alcohol were added to the oil mixture. The resulting oil mixture was heated to 62° to 30 75° C. The oil mixture was then added with vigorous mixing to the aqueous solution at a temperature of 66° C. over a period of three to five minutes. The resulting composition was cooled to 35° to 45° C. and homogenized by mixing with a high shear emulsifier or running through a homogenizer. The composition was further cooled to 25° to 30° C. The final composition was packaged in appropriate containers.

Examples 1–3 describe the use of the above method and the following ingredients in the parts by weight listed below to prepare formulations containing the compositions of the invention.

Example 1

| Ingredients | Parts By Weight |
| --- | --- |
| Enrofloxacin | 0.005–1.5 |
| Silver sulfadiazine(SSD) | 0.05–2.0 |
| Polysorbate 60 | 0.5–3.5 |
| Sorbitan monostearate | 0.5–3.0 |
| Cetyl stearyl alcohol | 0.5–3.0 |
| Benzyl alcohol | 1.0–3.0 |
| Miglyol Oil | 8–18 |
| Water | 89.4–68 |

Example 2

| Ingredients | Parts By weight |
| --- | --- |
| Enrofloxacin | 0.5–1.0 |
| Silver sulfadiazine(SSD) | 0.5–1.5 |
| Polysorbate 60 | 1.0–3.0 |
| Sorbitan monostearate | 1.0–2.0 |
| Cetyl stearyl alcohol | 1.0–2.0 |
| Benzyl alcohol | 1.5–2.5 |
| Miglyol Oil | 12–16 |
| Water | 85–74 |

Example 3

| Ingredients | Parts By weight |
| --- | --- |
| Enrofloxacin | 0.5 |
| Silver sulfadiazine(SSD) | 1.0 |
| Polysorbate 60 | 2.5 |
| Sorbitan monostearate | 1.5 |
| Cetyl stearyl alcohol | 1.5 |
| Benzyl alcohol | 2.0 |
| Miglyol Oil | 14.5 |
| Water | 76.5 |

Example 4

An in vitro microbiology study of the combination of the Enrofloxacin (quinolone) and sulfadiazine was conducted on multiple canine otic pathogens. The study was conducted under the National Committee for Clinical Laboratory Standards (NCCLS) guidelines employing ATCC control organisms for each agar plate tested. Initially, minimum inhibitory concentrations (MICs) were established for each active ingredient. Both enrofloxacin and silver sulfadiazine (SSD) were active on common dermal (otic) pathogens, based on MICs. Each has a different mode of action, though both are bactericidal. The different modes of action reduce the potential for resistance development. Additionally, Enrofloxacin was not effective on Malassezia or Candida at the concentrations tested. Silver sulfadiazine was effective on both. Evidence of Malassezia activity by silver sulfadiazine has not been reported previously.

Using MIC data, there were prepared agar plates containing serial dilutions of each antimicrobial in combination, using a standard checkerboard system. To identify possible interactions between the Enrofloxacin and the silver sulfadiazine, dilutions were prepared, that were for the most part, from three dilutions above to three dilutions below he MIC for each of the antimicrobials. The patterns of growth (inhibition) of the individual isolates, following exposure to the antimicrobials, were compared. Those of a single genera with the same response were grouped together. All isolates were then subjected to a mathematical calculation designed to indicate whether the antimicrobials were antagonistic, synergistic, or somewhere between. The standard calculation called a Fractional Inhibitory Concentration (FIC) Index is presented below $$\frac{X}{MIC_x} + \frac{Y}{MIC_y} = FIC_x + FIC_y = FIC \text{ index}$$

wherein X is equal to a concentration of drug X which is the lowest inhibitory concentration in its row of the checkerboard, and Y is equal to a concentration in its row of the checkerboard. FIC index equal to or less than 0.5 indicates synergism. FIC index equal to or greater than 2.0 indicates antagonism. FIC index equal to or greater than 0.5 but less than 2.0 indicates no effect.

For the purpose of comparison, the Enrofloxacin was also combined with clotrimazole. Clotrimazole has antifungal activity but essentially no activity on bacteria. The same series of pathogens were used to evaluate both antimicrobial combinations. FIC data from the study indicating response observed for the two combinations are presented below. (Table 1).

TABLE 1

Antimicrobial Range of Interaction

| Organism | Fractional Inhibitory Concentration Index | |
|---|---|---|
| | Enro* + SSD | Enro + Clotr |
| Pseudomonas aeruginosa (15)** | 0.507 to 0.75 | 1.167 to 2.67 |
| Staphylococcus intermedius (12) | 1.5 | 1.5 |
| Escherichia coli (7) | 0.36 to 1.5 | 0.8 to 1.8 |
| Klebsiella pneumoniae (5) | 0.62 to 1.5 | 1.8 to 2.3 |
| Beta-hemol Streptococcus (9) | 0.625 to 1.5 | 0.75 to 2.25 |
| Malassezia sp (12) | 1.5 | 0.56 to 1.5 |
| Candida sp (4) | 1.5 to 1.75 | 1.5 |

*Drug abbreviations are:
Enro = Enrofloxacin
SSD = Silver Sulfadiazine
Clotr = Clotrimazole
**Numbers in parenthesis indicates numbers of isolates tested.

As to the isolates reported above, the combination of the Enrofloxacin and silver sulfadiazine had no values in the antagonistic category. The FIC indices for many of the bacterial isolates were less than 1.0 showing a clear tendency towards additive effect. A few calculations showed synergism. There was less of a tendency to an additive effect with Malassezia and Candida.

The additive effect of the Enrofloxacin and the silver sulfadiazine could not have been predicted because the combination of antimicrobials with different modes of activity could have just as easily demonstrated antagonism. Antagonism was clearly demonstrated, for example, with the combination of Enrofloxacin and Clotrimazole. In three of the five bacterial genera reported above, a score of greater than 2 was calculated. Clotrimazole does not have antibacterial activity, yet the data indicated that the drug apparently interfered with the antibacterial effect of the Enrofloxacin.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of treating an otic infection in an animal comprising administering a composition that is useful in treating otic infections comprising an antimicrobial and silver sulfadiazine in a therapeutically effective combination to treat otic infections.

2. The method of claim 1 wherein the composition is administered in a pharmaceutically effective amount.

3. The method of claim 1 wherein the composition is administered on a twice daily basis.

* * * * *